United States Patent [19]
Pagan

[11] Patent Number: 6,095,144
[45] Date of Patent: Aug. 1, 2000

[54] LARYNGEAL MASK ASSEMBLIES

[75] Inventor: Eric Pagan, Hythe, United Kingdom

[73] Assignee: Smiths Industries Public Limited Company, London, United Kingdom

[21] Appl. No.: 09/069,938

[22] Filed: Apr. 30, 1998

[30] Foreign Application Priority Data

May 3, 1997 [GB] United Kingdom .................... 9709297

[51] Int. Cl.⁷ .................................................. A61M 16/00
[52] U.S. Cl. .................................. 128/207.15; 128/207.14
[58] Field of Search ......................... 128/200.26, 207.14, 128/207.15, 206.29, 911, 912, DIG. 26; 604/96; 600/187, 188, 190, 194, 199

[56] References Cited

U.S. PATENT DOCUMENTS

| 4,329,983 | 5/1982 | Fletcher . |
| 4,995,388 | 2/1991 | Brain . |
| 5,297,547 | 3/1994 | Brain . |
| 5,303,697 | 4/1994 | Brain .................................. 128/200.26 |
| 5,896,858 | 4/1999 | Brain .................................. 128/207.15 |
| 5,967,859 | 8/1999 | Augustine et al. ................. 128/207.15 |

FOREIGN PATENT DOCUMENTS

| 2205499 | 12/1988 | United Kingdom . |
| 2317342 | 3/1998 | United Kingdom . |
| 97/12641 | 4/1997 | WIPO . |

*Primary Examiner*—Aaron J. Lewis
*Assistant Examiner*—Teena Mitchell
*Attorney, Agent, or Firm*—Pollock, Vande Sande & Amernick

[57] ABSTRACT

A laryngeal mask assembly has a tubular shaft with a mask portion formed by a resilient skirt towards its patient end, which seals with tissue in the region of the hypopharynx. An inflatable cuff, with several annular reinforcing members, projects axially at the patient end of the assembly into the laryngeal inlet. Towards its patient end, the cuff has a flap that normally closes the passage through the cuff and prevents entry of the epiglottis. A pull cord attached with the flap enables the flap to be pulled to one side, deflecting the epiglottis and opening the passage through the cuff.

11 Claims, 3 Drawing Sheets

LARYNGEAL MASK ASSEMBLIES

BACKGROUND OF THE INVENTION

This invention relates to laryngeal mask assemblies.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305,743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561 and GB 9603555.

Laryngeal masks have several advantages over endotracheal tubes, which are longer and seal with the trachea below the vocal folds.

SUMMARY OF THE INVENTION

It is an object of the present invention to provide an improved laryngeal mask assembly.

According to one aspect of the present invention there is provided a laryngeal mask assembly comprising a tubular shaft having a mask portion towards its patient end, the mask portion being adapted to seal with tissue in the region of the hypopharynx, the assembly additionally including an expansible tubular cuff member extending substantially axially of the tubular shaft beyond the mask portion into the laryngeal inlet.

The cuff member preferably includes a deflectable member at its patient end that, in one position, prevents entry of the epiglottis into the opening at the patient end of the assembly and, in another position, deflects the epiglottis away from the opening at the patient end of the assembly. The assembly may include a pull cord attached with the deflectable member by which the deflectable member can be moved from the one position to the other position.

According to another aspect of the present invention there is provided a laryngeal mask assembly comprising a tubular shaft having a mask portion towards its patient end, the mask portion being adapted to seal with tissue in the region of the hypopharynx, the assembly additionally including a cuff member that can be changed from a first state where it prevents entry of the epiglottis into the patient end of the assembly to a second state where it deflects the epiglottis away from the opening at the patient end of the assembly.

The mask portion is preferably a non-inflatable resilient skirt. The cuff member is preferably inflatable. Alternatively, the cuff member is a resilient funnel-shape member. The cuff member may include one and preferably a plurality of annular reinforcing members arranged to keep open a central passage through a part of the cuff member.

A laryngeal mask assembly according to the present invention, will now be described, by way of example, with reference to the accompanying drawings.

DETAILED DESCRIPTION OF THE PREFERRED EMBODIMENTS

Figure 1:
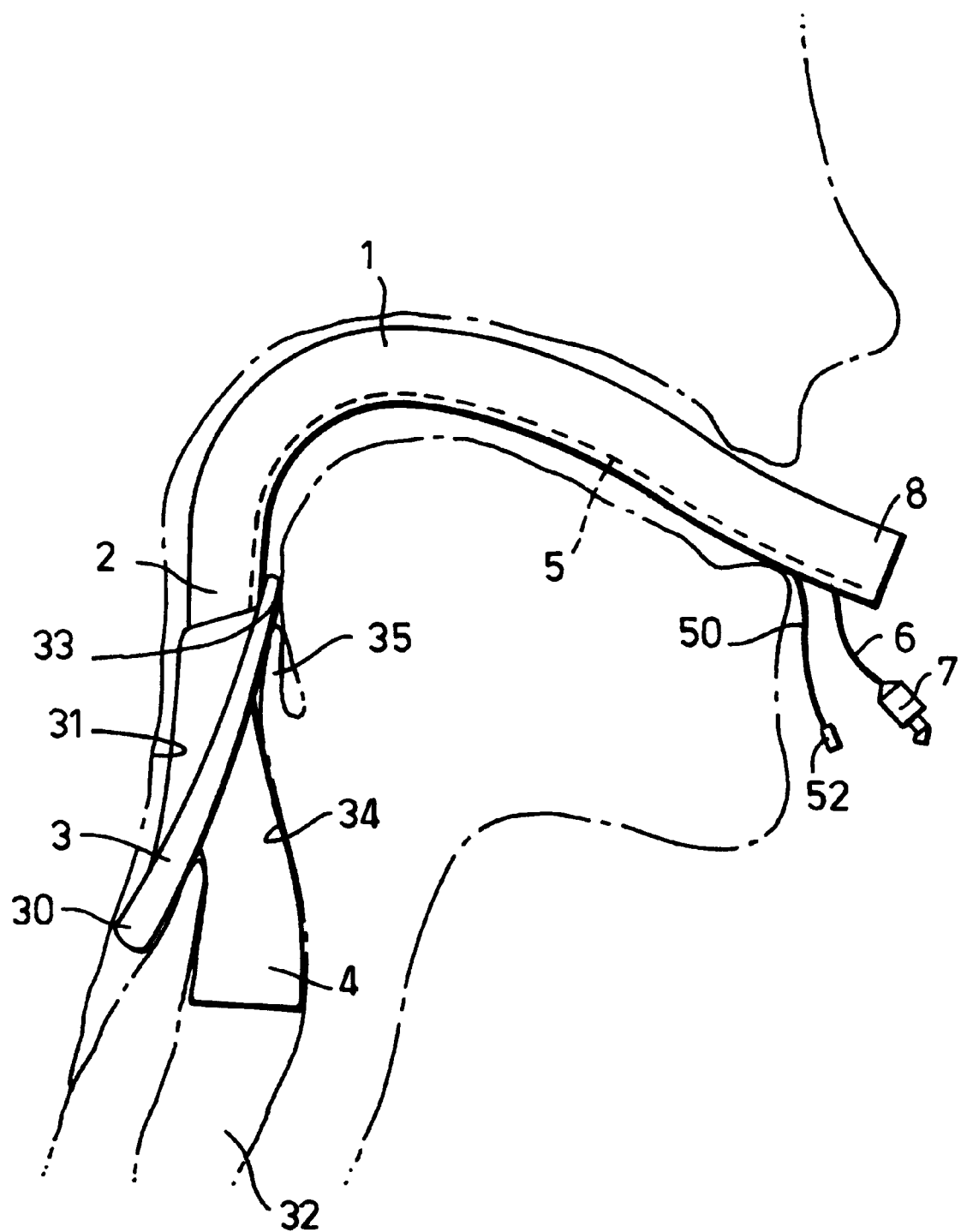
FIG. 1 is a side elevation view of the laryngeal mask assembly in use.

With reference first to FIGS. 1 and 2, the laryngeal mask assembly has a tubular shaft 1 of a bendable plastics material, such as PVC, which is bent to conform to the anatomy of the patient. At its patient end 2, the assembly has a laryngeal mask member 3 and an inflatable laryngeal cuff 4, which will be described in detail later. The interior of the laryngeal cuff 4 communicates with an inflation lumen 5 extending along the length of the shaft 1, within its wall, which connects to a small bore inflation line 6 terminated by a combined inflation indicator and connector 7. The machine end 8 of the assembly projects a short distance from the patient's mouth.

The laryngeal mask member may be of the conventional inflatable kind, such as described in GB 2205499, in which case it would communicate with a separate inflation line. As shown, however, in the present example, the mask 3 is non-inflatable and in the form of a thin, flexible, resilient skirt 30 of elliptical shape attached to the outside of the shaft 1 at its patient end 2. The peripheral shape of the mask 3 is chosen so that it conforms to and seals with tissue in the region of the hypopharynx 31, so as to form a seal around the circumference of the opening 33 of the laryngeal inlet 34.

Figure 2A:
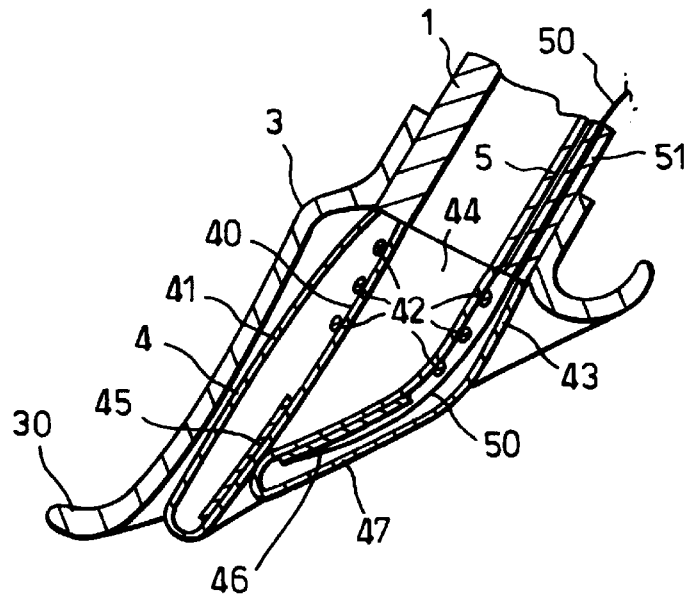
FIG. 2A is an enlarged sectional side elevation view of the patient end of the mask assembly showing the laryngeal cuff before introduction.

The patient end 2 of the shaft 1 supports the laryngeal cuff 4, which projects axially beyond the patient end of the shaft. The cuff 4 is of cylindrical shape with an inner wall 40 and an outer wall 41. The inner wall 40 carries several annular reinforcing members 42 spaced from one another along a rear portion 43 of the cuff, which act to keep open a central passage 44 through the rear part of the cuff. Towards its forward end, the cuff 4 has two curved plates 45 and 46 diametrically opposite one another, which serve to stiffen the forward portion of the cuff. The forward end of the cuff 4 is formed, as shown in FIG. 2A, so that its resilience urges a flap region 47, extending around approximately half the circumference of the cuff, towards the opposite side of the cuff so that the forward end of the cuff lies approximately along the plane containing the forward surface of the skirt 30. It can be seen that, in this state, the opening to the forward end of the shaft 1 is closed.

Figure 2B:
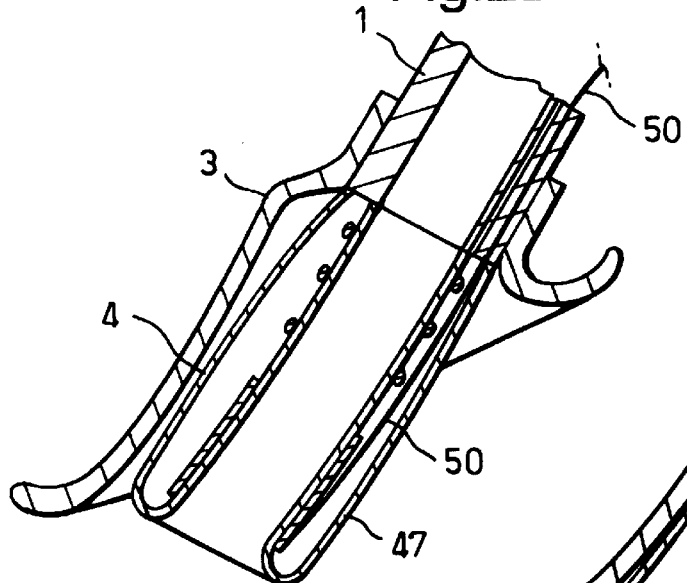
FIGS. 2B and 2C are enlarged sectional side elevation view of the patient end of the mask assembly showing the laryngeal cuff in an intermediate and expanded state respectively.

The assembly also includes a pull cord 50 extending within the cuff 4 and attached at its forward end to the flap region 47. The cord 50 extends along the length of the assembly, through a passage 51 extending through the shaft 1. The rear end 52 of the cord 50 extends from the machine end of the assembly, as shown in FIG. 1. The cord 50 is arranged so that, when it is pulled, it pulls the flap region 47 away from the opposite side of the cuff, as shown in FIG. 2B. In this position, the length of the cuff 4 is such that it projects just beyond the forward, patient end of the mask 3.

The mask assembly is introduced in any of the conventional ways used with laryngeal masks, so that the mask 3 is located to extend around the opening 33 of the laryngeal inlet 34. The assembly is introduced with the cuff 4 in the state shown in FIG. 2A, that is, with the flap region 47 covering the opening to the cuff. This prevents the epiglottis 35 from entering the patient end of the assembly during insertion. The clinician then pulls the cord 50 so that the flap 47 swings down to the right, opening the passage through the assembly and displacing the epiglottis to one side, if this should be folded down across the patient end of the mask 3. This also causes the patient end 2 of the shaft and the laryngeal cuff 4 to project into the laryngeal inlet. The clinician then introduces a measured volume of air via the connector 7 into the cuff 4 so that it expands axially and radially into the laryngeal inlet 34. The cord 50 may be clipped in some way at its machine end, so that flap 47 remains open, or the inflation of the cuff with the introduced air may be sufficient by itself to keep the flap open.

Figure 2C:
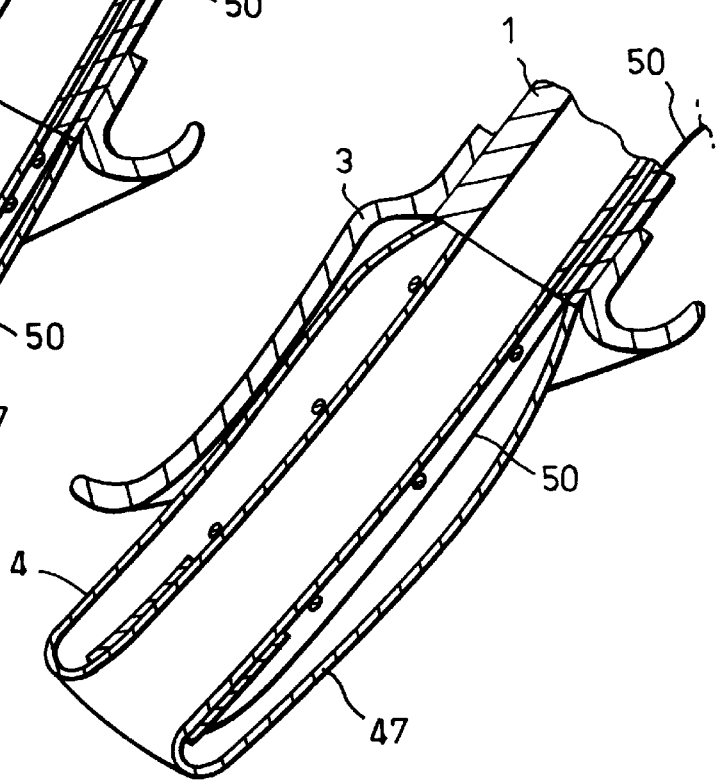

When the cuff 4 is inflated, it extends both axially and radially outwards to a position shown in FIG. 2C. In this position, the cuff 4 extends into the laryngeal inlet 34 but does not extend within the larynx 32 itself. The radial expansion of the cuff causes it to seal with tissue in the laryngeal inlet.

Because the laryngeal cuff 4 provides an effective seal, it is not essential that the seal provided by the laryngeal mask 3 be complete. The assembly of the present invention can provide an improved seal compared with conventional laryngeal masks and has the advantage of ensuring that the epiglottis does not present any obstruction.

Various modifications are possible. For example, the laryngeal cuff need not be expanded by positive air pressure but could be filled with a resilient material, such as a foam, and be reduced in volume for introduction or removal by a negative pressure, or some form of mechanical arrangement, such as pull cords. The mask need not seal around the laryngeal inlet but could seal in the pharyngeal region.

Figure 3A:
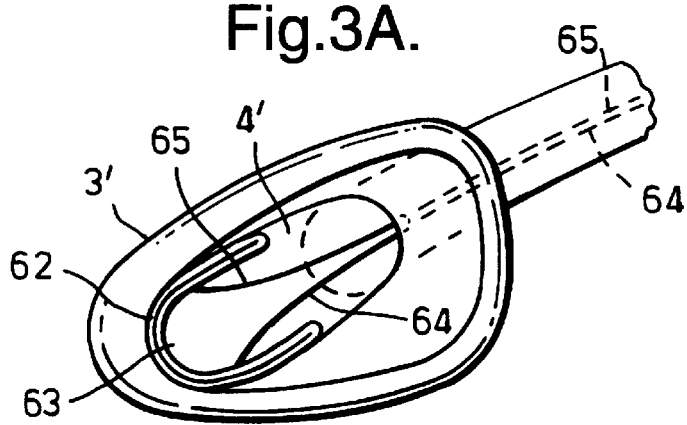
FIGS. 3A is a perspective view of the patient end of an alternative assembly before introduction.
Figure 3B:
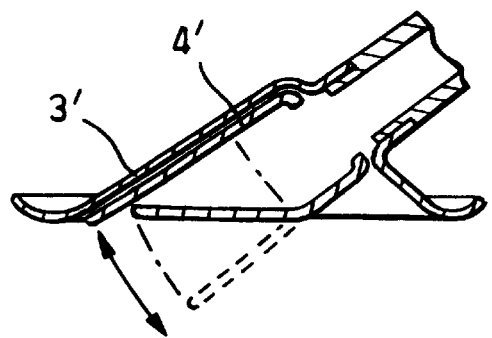
FIG. 3B. is a sectional side elevation view of the assembly of FIG. 3A before introduction.
Figure 3C:
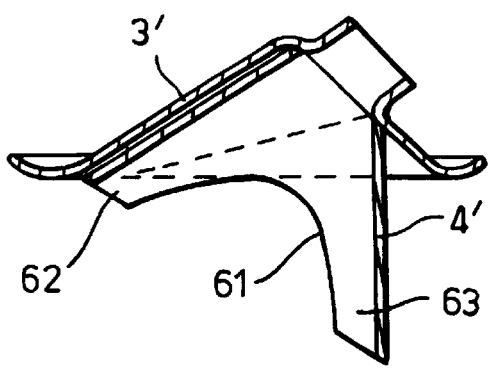
FIG. 3C is a sectional side elevation view of the assembly as expanded after introduction.
Figure 3D:
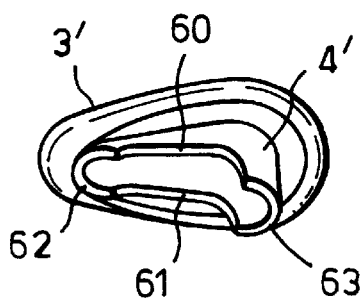
FIG. 3D is a perspective view of the patient end of the assembly as expanded after introduction.

In another alternative arrangement, the assembly has a non-inflatable cuff that projects within the laryngeal inlet 34 but does not make a complete seal with it. Such an assembly is shown in FIGS. 3A to 3D. The assembly has a mask 3' of the same kind as shown in FIGS. 1 and 2 but, in place of the inflatable cuff 4 it has a cuff 4' formed of a resilient material, which, in its natural state, as shown in FIGS. 3C and 3D, has the shape of a flat funnel. The cuff 4' is divided by two recesses 60 and 61 into two lateral portions 62 and 63. For introduction into the patient, one of the lateral portions 63 is inverted into the other 62, as shown in FIG. 3A, so that the patient end of the cuff is closed and of semi-cylindrical shape. In this position, the cuff 4' does not project beyond the mask 3'. Two pull cords 64 and 65 are attached to the inverted portion 63 of the cuff 4' so that, once it is in position in the patient, the cords can be pulled, to open out the cuff to its natural shape shown in FIGS. 3B to 3D. This again causes the epiglottis 35 to be deflected out of the way, should it be located across the end of the mask 3'. The natural resilience of the cuff 4' urges the two portions 62 and 63 against opposite sides of the laryngeal inlet.

What I claim is:

1. A laryngeal mask assembly comprising: a tubular shaft with a patient end and a machine end; a mask portion towards said patient end of said tubular shaft, said mask portion being shaped to seal, in use, with tissue in the region of the hypopharnx, and a tubular cuff member attached at one end with said laryngeal mask assembly, said tubular cuff member extending substantially axially of said tubular shaft beyond said mask portion into the laryngeal inlet, and wherein an opposite end of said cuff member is axially expandable relative to said mask and forms an extension of said tubular shaft.

2. A laryngeal mask assembly according to claim 1, wherein said cuff member includes a deflectable member at its patient end that, in one position, prevents entry of the epiglottis into the patient end of said assembly and, in another position, deflects the epiglottis away from the patient end of said laryngeal mask assembly.

3. A laryngeal mask assembly according to claim 2, wherein said laryngeal mask assembly includes a pull cord attached with said deflectable member, and wherein said pull cord is operable to move said deflectable member from said one position to said other position.

4. A laryngeal mask assembly according to claim 1, wherein said cuff member includes at least one annular reinforcing member arranged to keep open a central passage through a part of said cuff member.

5. A laryngeal mask assembly according to claim 4, wherein said cuff member includes a plurality of said annular reinforcement members.

6. A laryngeal mask assembly comprising: a tubular shaft with a patient end and a machine end; a mask portion towards said patient end of said tubular shaft, said mask portion being adapted to seal with tissue in the region of the hypopharynx; and a cuff member attached at one end with said laryngeal mask assembly and forming an extension of said tubular shaft, said cuff member being changeable from a first state where it prevents entry of the epiglottis into the patient end of said laryngeal mask assembly to a second state where it deflects the epiglottis away from the patient end of said assembly.

7. A laryngeal mask assembly according to claim 1 or 6, wherein said mask portion is a non-inflatable resilient skirt.

8. A laryngeal mask assembly according to claim 1 or 6, wherein said cuff member is inflatable.

9. A laryngeal mask assembly according to claim 1 or 6, wherein said cuff member is a resilient funnel-shape member.

10. A laryngeal mask assembly comprising: a tubular shaft with a patient end and a machine end; a mask portion towards said patient end of said tubular shaft, said mask portion being shaped to seal, in use, with tissue in the region of the hypopharynx; and an inflatable tubular cuff member, said cuff member having an axial passage extending therethrough, and said cuff member extending substantially axially of said tubular shaft beyond said mask portion into the laryngeal inlet, said cuff member having a flap member folded over a patient end of said passage through said cuff member to prevent entry of the epiglottis to said cuff member; and a pull cord attached with said flap member and extending to said machine end of said shaft, said pull cord operable to deflect said flap member and open the passage through said cuff member.

11. A laryngeal mask assembly comprising: a tubular shaft with a patient end and a machine end; a mask portion towards said patient end of said tubular shaft, said mask portion being shaped to seal, in use, with tissue in the region of the hypopharynx; and a resilient cuff member extending substantially axially of said tubular shaft beyond said mask portion into the laryngeal inlet, said cuff member having a funnel shape with two opposite sides that are deflectable between a first position in which said sides closely engage one another and a second position in which said sides are spaced from one another and there is an open passage along the cuff member; and a pull cord attached with said cuff member and extending to said machine end of said shaft, said pull cord operable to deflect said sides of said cuff member from said first position to said second position.

* * * * *